United States Patent [19]

White et al.

[11] Patent Number: 4,784,996

[45] Date of Patent: Nov. 15, 1988

[54] PYRIMIDOINDOLES USEFUL AS HYPOGLYCAEMICS

[75] Inventors: Alan C. White, Englefield Green; Ian A. Cliffe, Cippenham; Richard S. Todd, Burnham, Nr. Slough, all of England

[73] Assignee: John Wyeth & Brother Ltd., Maidenhead, England

[21] Appl. No.: 23,337

[22] Filed: Mar. 9, 1987

[30] Foreign Application Priority Data

Mar. 13, 1986 [GB] United Kingdom ............... 8606253

[51] Int. Cl.⁴ .................. A61K 31/505; C07D 487/04
[52] U.S. Cl. ..................................... 514/267; 544/252
[58] Field of Search .......................... 544/252; 514/267

[56] References Cited

U.S. PATENT DOCUMENTS 2,984,666  5/1961  Bortnick et al. ............... 544/252
3,634,426  1/1972  Eberle ........................... 540/561 X
3,891,644  6/1975  White ............................. 544/252

FOREIGN PATENT DOCUMENTS 1366133  9/1974  United Kingdom ............... 544/252

Primary Examiner—Donald G. Daus
Assistant Examiner—Diana G. Rivers
Attorney, Agent, or Firm—Richard K. Jackson

[57] ABSTRACT

Compounds of formula

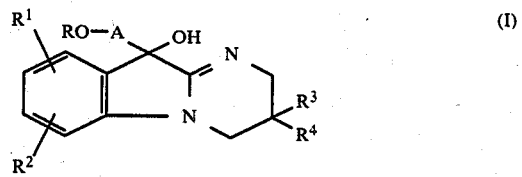

wherein A represents a lower alkylene chain optionally containing one double or triple bond, RO represents (lower)alkoxy, aryl(lower)alkoxy, hydroxy or protected hydroxy, $R^1$ and $R^2$ which may be the same or different each represent hydrogen, hydroxyl, lower alkyl, lower alkoxy, halo(lower)alkyl, halogen, amino or mono- or di(lower)alkylamino and $R^3$ and $R^4$ each independently represent hydrogen or lower alkyl and their pharmaceutically acceptable acid addition salts are useful as hypoglycaemics or as intermediates for hypoglycaemics.

17 Claims, No Drawings

PYRIMIDOINDOLES USEFUL AS HYPOGLYCAEMICS

This invention relates to pyrimidoindoles, to processes for their preparation, to their use and to pharmaceutical compositions containing them.

The novel compounds of the present invention are pyrimidoindoles of the general formula (I)

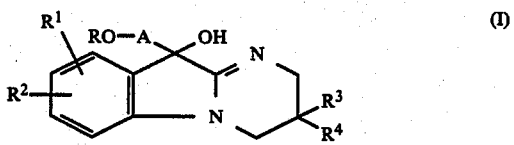

and their pharmaceutically acceptable acid addition salts. In the formula, A represents a lower alkylene chain optionally containing one double or triple bond, RO represents (lower)alkoxy, aryl(lower)alkoxy, hydroxy or protected hydroxy, $R^1$ and $R^2$ which may be the same or different each represent hydrogen, hydroxyl, lower alkyl, lower alkoxy, halo(lower)alkyl, halogen, amino or mono- or di(lower)alkylamino and $R^3$ and $R^4$ each independently represent hydrogen or lower alkyl.

The term "lower" as used herein means that the radical referred to contains 1 to 6 carbon atoms. Preferably such radicals contain 1 to 4 carbon atoms. For example, a lower alkyl group may be methyl, ethyl, propyl or butyl and a lower alkoxy may be methoxy, ethoxy, propoxy or butoxy.

When RO is an aryl(lower)alkoxy group, the aryl radical is preferably a phenyl group which may optionally be substituted by, for example, the substituents defined above in respect of $R^1$ and $R^2$; for example RO may represent an optionally substituted benzyloxy group. When RO is a protected hydroxy group, the group may be, for example, tetrahydropyranyloxy or trialkylsiloxy (eg trimethylsiloxy); benzyloxy may also be used as a protecting group. Preferably RO is (lower)alkoxy.

A may be a straight or branched lower alkylene chain optionally containing a double or triple bond. Preferably A is a branched or straight chain saturated alkylene group containing 3 to 5 carbon atoms. Examples of suitable RO—A— groups include 3- or 4-methoxybutyl, 4-ethoxybutyl, 3-methoxy-2-methylpropyl and 3-hydroxy-1-propynyl.

Preferred examples of $R^1$ and $R^2$ residues include hydrogen, lower alkyl (e.g. methyl, ethyl propyl and butyl), lower alkoxy (e.g. methoxy, ethoxy, propoxy and butoxy), halo(lower)alkyl (e.g. trifluoromethyl) and halogen (e.g. chlorine and bromine).

Preferably both $R^3$ and $R^4$ represent lower alkyl (e.g. methyl).

Examples of preferred compounds of the invention are:
3,3-dimethyl-10-hydroxy-10-(4-methoxybutyl)-2,3,4,10-tetrahydropyrimido[1,2-a]indole
2,3,4,10-tetrahydro-10-hydroxy-3,3-dimethyl-10-(3-methoxy-2-methylpropyl)pyrimido[1,2-a]indole
2,3,4,10-tetrahydro-10-hydroxy-10-(3-methoxybutyl)-3,3-dimethylpyrimido[1,2-a]indole
8-chloro-10-hydroxy-10-(4-methoxybutyl)-2,3,4,10-tetrahydropyrimido[1,2-a]indole
10-(4-benzyloxybutyl)-2,3,4,10-tetrahydro-10-hydroxy-3,3-dimethylpyrimido[1,2-a]indole
10-(4-ethoxybutyl)-2,3,4,10-tetrahydro-10-hydroxy-3,3-dimethylpyrimido[1,2-a]indole
2,3,4,10-tetrahydro-10-hydroxy-10-(3-methoxybutyl)-pyrimido[1,2-a]indole
10-hydroxy-10-(3-hydroxy-1-propynyl)-2,3,4,10-tetrahydropyrimido[1,2-a]indole
and pharmaceutically acceptable salts thereof.

The compounds of the invention in which RO represents (lower)alkoxy, aryl(lower)alkoxy or protected hydroxy may be prepared by a process in which a ketone of general formula (II)

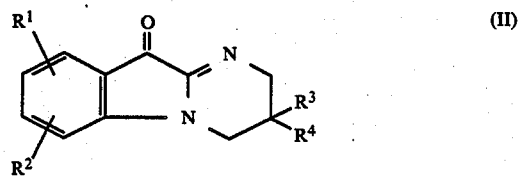

where $R^1$, $R^2$, $R^3$ and $R^4$ have the meanings given above is reacted with an organometallic compound containing a RO-A-residue where A is as defined above and RO is (lower)alkoxy, aryl(lower)alkoxy or protected hydroxy. The organometallic compound is preferably a lithium compound of formula RO-A.Li or a Grignard reagent of formula RO-A.MgY where A is as defined above, RO represents (lower)alkoxy, aryl(lower)alkoxy or protected hydroxy and Y is halogen. The reaction with the organometallic compound may be carried out in an inert organic solvent.

The ketones of general formula (II) are known in the literature or may be prepared by known processes, for example those disclosed in U.K. Specification No. 1,366,133.

An alternative method of preparing the compounds of the invention in which RO represents (lower)alkoxy, aryl(lower)alkoxy, or protected hydroxy and A is a saturated lower alkylene chain comprises cyclodehydrating an indole derivative of the general formula (III)

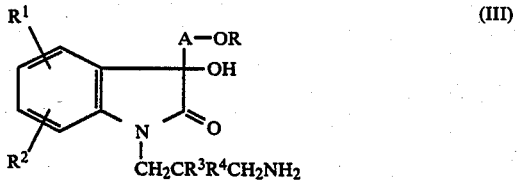

wherein $R^1$, $R^2$, $R^3$ and $R^4$ have the meanings given above, A is a saturated lower alkylene chain and RO is (lower)alkoxy, aryl(lower)alkoxy or protected hydroxy.

The compound of general formula (III) in its free base form or as an acid addition salt thereof may be cyclodehydrated to the compound of general formula (I) by heating it, for example, in an inert organic solvent. It is preferred to carry out the cyclisation in the presence of a catalytic amount of an acid catalyst, e.g. p-toluene sulphonic acid or benzene sulphonic acid.

The indole compounds of general formula (III) and their acid addition salts can be prepared by the hydrogenation of a nitrile compound of general formula (IV)

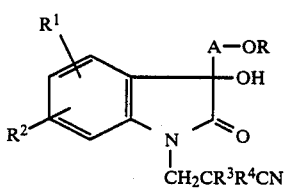

wherein A, $R^1$, $R^2$, $R^3$, $R^4$ and $R^5O$ have the meanings given above in connection with formula (III).

The hydrogenation may be carried out in the presence of a hydrogenation catalyst. Elevated temperatures and pressures may be employed. However, if the compound of formula (IV) contains any substituents $R^1$ and $R^2$, such as halogen atoms, which are liable to be effected by drastic hydrogenation conditions, the hydrogenation should be carried out under mild conditions. For example, a nickel catalyst [such as Raney nickel, e.g. Raney nickel W2 (Org. Syn. Coll. Vol. III, 1955, 181)] can be employed, e.g. in presence of ammonia and ethanol, and the hydrogenation carried out at relatively low pressures and temperatures.

The compounds of general formula (III) need not be isolated from the hydrogenation reaction medium and hence the compounds of formula (I) may be prepared by hydrogenation of the nitrile compounds of general formula (IV).

The nitrile compounds of general formula (IV) can be prepared from oxindoles of general formula (V)

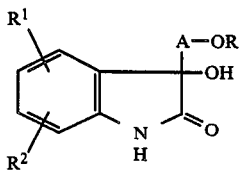

wherein $R^1$, $R^2$ and RO have the meanings given above in connection with formula III. For example, a compound of formula (IV) in which $R^3$ and $R^4$ are hydrogen can be prepared by Michael addition of the oxindole to acrylonitrile. For example, the oxindole can be reacted with acrylonitrile in an inert solvent, preferably in presence of a basic catalyst. A particularly suitable basic catalyst is benzyltrimethylammonium hydroxide (Triton B) used as a 40% solution in water. A compound of formula (IV) in which $R^3$ and/or $R^4$ are independently lower alkyl or in which $R^3$ and $R^4$ together with the carbon atom to which they are attached represent cycloalkyl can be prepared by reacting the oxindole with an appropriately 2-substituted-3-halopropionitrile in the presence of a base.

The oxindoles of general formula (V) are known compounds or they may be prepared by known methods. For example an isatin of the general formula (VI)

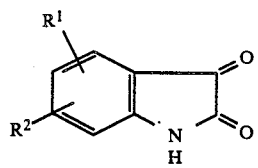

wherein $R^1$ and $R^2$ have the meanings given above may be reacted with a Grignard reagent of general formula (VII)

ROA.MgBr  (VII)

or a lithium compound of formula ROA.Li wherein A and RO have the meaning given above in connection with formula (III).

The indole derivatives of general formula (III) can be prepared by an alternative method which comprises removing the protecting group from a corresponding compound of formula (III) in which the amino group is protected, e.g. hydrolysing a phthalimide derivative of general formula (VIII)

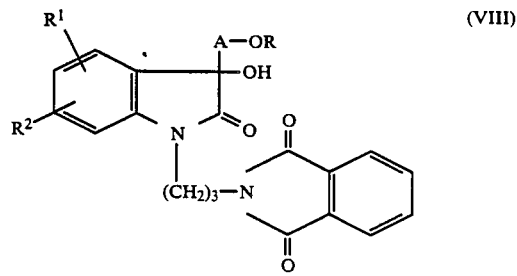

wherein $R^1$, $R^2$, A and OR are as hereinbefore defined with reference to formula (III).

The hydrolysis of the phthalimide derivative of general formula (VIII) can be carried out in the presence of, e.g. acid, base or hydrazine as in the Gabriel synthesis.

The compound of formula (III) in which the amino group is protected may be prepared by condensing an oxindole of general formula (V) above with a 1-protected amino-3-halopropane. For example the phthalimide derivative of general formula (VIII) may be prepared by condensation of an oxindole of general formula (V) as given above, with N-(3-halopropyl)phthalimide, e.g. N-(3-bromiopropyl)phthalimide. The condensation can be effected in presence of a basic catalyst such as sodium hydride in, for example, an organic solvent e.g. dimethylformamide or toluene.

The compounds of the invention in which RO represents hydroxy may be prepared by de-etherification of the compounds of formula (I) in which RO is (lower)alkoxy or aryl(lower)alkoxy or removing the protecting group, by methods known in the art, from a compound of formula I in which RO is a protected hydroxy group. In a preferred method, a compound of formula (I) in which RO is benzyloxy is subjected to hydrogenolysis in presence of a hydrogenation catalyst.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of the invention possess at least one asymmetric carbon atom and hence can exist in various stereochemical forms. The stereochemical forms can be separated or isolated by standard procedures. For example resolution of a racemic final product or intermediate may be carried out by known procedure so as to give the product as an optically active enantiomorph.

The compounds of the present invention in which RO represents (lower)alkoxy, aryl(lower)alkoxy and hydroxy possess pharmacological activity. For example, the compounds in general possess hypoglycaemic activity and hence are of value in the treatment of diabetes. The compounds of the invention are tested for hypoglycaemic activity by a standard procedure in which the compounds are administered to rats and the blood glucose concentration is determined prior to administration and at various times after dosage. When 2,3,4,10-tetrahydro-10-hydroxy-10-(3-methoxybutyl)-3,3-dimethylpyrimido[1,2-a]indole, a representative compound of the invention, was tested by this procedure at 20, 50 and 100 mg/kg p.o. the plasma glucose concentration was found to be respectively 79%, 73% and 54% of control animals (i.e. rats administered vehicle alone) at 2 hours after administration.

The invention further provides a compound of formula (I) in which RO represents (lower)alkoxy, aryl(lower)alkoxy or hydroxy or a pharmaceutically acceptable acid addition salt for use as a hypoglycaemic in a mammal.

The invention also provides a pharmaceutical composition comprising a compound of general formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intrasmuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such composition in package form. The quantity of the active ingredient in unit dose of composition may be varied or adjusted from 0.5 mg or less to 750 mg or more, according to the particular need and the activity of the active ingredient. The invention also includes the compounds in the absence of the carrier where the compounds are in unit dosage form.

The following Examples illustrate the invention;

EXAMPLE 1

3,3-Dimethyl-10-hydroxy-10-(4-methoxybutyl)-2,3,4,10-tetrahydropyrimido[1,2-a]indole A solution of 1-bromo-4-methoxybutane (6.26 g) in diethyl ether (23 ml) was added dropwise to stirred magnesium turnings (0.9 g) under nitrogen, at a rate sufficient to maintain reflux. The mixture was stirred for a further 45 min., then a solution of 3,4-dihydro-3,3-dimethylpyrimido[1,2-a]indole-10(2H)-one (1.6 g) in 1,2-dichloroethane (75 ml) was added dropwise. The mixture was stirred for 30 min., then poured into aqueous ammonium chloride solution and extracted with chloroform (2×100 ml). The chloroform extracts were combined, dried (MgSO$_4$) and evaporated under reduced pressure giving an orange solid. Trituration from ethyl acetate, followed by recrystallisation from ethyl acetate gave the title compound (1.2 g(. Addition of ethereal hydrogen chloride to a solution of the free base in methanol, followed by evaporation of the solvents and crystallisation of the resulting solid from propan-2-ol gave the hydrochloride salt (0.6 g), m.p. 188°–190°.

Found: C, 63.9; H, 8.2; N, 8.1%. $C_{18}H_{26}N_2O_2$.HCl requires: C, 63.8; H, 8.0; N, 8.3%.

EXAMPLE 2

2,3,4,10-Tetrahydro-10-hydroxy-3,3-dimethyl-10-(3-methoxy-2-methylpropyl)pyrimido[1,2-a]indole Approximately one quarter of a solution of 1-bromo-3-methoxy-2-methylpropane (5.65 g) in diethyl ether (10 ml) was added to stirred magnesium turnings (0.97 g) under nitrogen, followed by three drops of 1,2-dibromoethane. The mixture was heated, and when the reaction commenced, the remaining solution of 1-bromo-3-methoxy-2-methylpropane in ether was added at such a rate as to maintain reflux. The mixture was heated to reflux for a further 15 min., cooled to room temperature, and a solution of 3,4-dihydro-3,3-dimethylpyrimido[1,2-a]indol-10(2H)-one (2.91 g) in 1,2-dichloroethane (50 ml) added dropwise. After 1 hour the reaction mixture was poured into water (200 ml), extracted with chloroform (2×100 ml), the chloroform extracts combined, dried (MgSO$_4$) and the solvents evaporated under reduced pressure to give a solid (2.3 g). The solid was crystallised from ethyl acetate, giving the title compound (1.1 g). The mother liquid was evaporated under reduced pressure giving a crude solid which was triturated from ethyl acetate, giving more of the title compound (0.45 g). Ethereal hydrogen chloride was added to a solution of the combined solids (1.55 g) in methanol. The solvents were removed under reduced pressure to give the title compound as the hydrochloride salt (1.58 g), m.p. 154.5°–155.5°.

Found: C, 63.3; H, 8.0; N, 8.3%. C$_{18}$H$_{26}$N$_2$O$_2$.HCl.¼H$_2$O requires: C, 63.0; H, 8.1; N, 8.2%.

EXAMPLE 3

2,3,4,10-Tetrahydro-10-hydroxy-10-(3-methoxybutyl)-3,3-dimethylpyrimido[1,2-a]indole A solution of 1-bromo-3-methoxybutane (4.75 g) in diethyl ether (10 ml) was added to magnesium turnings (1.03 g) in diethyl ether (10 ml) under nitrogen at such a rate as to maintain reflux. After 45 minutes at reflux temperature the solution was cooled to 0° and a solution of 3,4-dihydro-3,3-dimethylpyrimido[1,2-a]indol-10(2H)-one (3.03 g) in 1,2-dichloroethane (50 ml) added dropwise. The cooling bath was removed and after 0.5 hour the solution was poured into saturated aqueous NH$_4$Cl (100 ml) and the mixture extracted with chloroform (3×100 ml). The chloroform extracts were dried (MgSO$_4$) and evaporated under reduced pressure to give a solid (3.7 g). The solid was washed with a small quantity of ethyl acetate then crystallised from ethyl acetate, giving the title compound (2.29 g). A solution of the free base in methanol was treated with ethereal HCl, the solvents evaporated under reduced pressure and the gum triturated with ether to give the title compound hydrochloride, m.p. 179°–186°.

Found: C, 62.9; H, 8.2; N, 8.0%. C$_{18}$H$_{26}$N$_2$O.HCl.¼H$_2$O requires: C, 63.0; H, 8.1; N, 8.2%.

EXAMPLE 4

8-Chloro-10-hydroxy-10-(4-methoxybutyl)-2,3,4,10-tetrahydropyrimido[1,2-a]indole A Grignard reagent was prepared from 4-methoxybutyl bromide (5 g) and magnesium (0.72 g) in dry ether (25 ml). After cooling with an ice-bath, under a blanket of nitrogen, a solution of 8-chloro-3,4-dihydropyrimido[1,2-a]indol-10(2H)-one (2.2 g) in dichloromethane (25 ml) was added slowly. When addition was complete the mixture was stirred at room temperature for 3 hours. It was poured onto saturated aqueous NH$_4$Cl, the layers were separated and the aqueous phase extracted with dichloromethane. The combined organic phases were washed with water and dried (MgSO$_4$). Filtration and evaporation gave an orange solid, which was triturated with boiling ethyl acetate, cooled, filtered and the crystals were washed with hexane. The crystals were suspended in boiling ethanol and acidified with ethanolic HCl. Evaporation of the solution gave a solid which crystallised from isopropanol. Two crops were combined and dried at 50°/1 mm to give pure 8-chloro-10-hydroxy-10-(4-methoxybutyl)-2,3,4,10-tetrahydropyrimido[1,2-a]indole, hydrochloride quarter hydrate (2.28 g) as buff-cream crystals, m.p. 218°–221° (dec).

Found: C, 55.2; H, 6.5; N, 7.8%. C$_{16}$H$_{21}$ClN$_2$O$_2$.HCl.¼H$_2$O requires: C, 54.9; H, 6.5; N, 8.0%.

EXAMPLE 5

10-(4-Benzyloxybutyl)-2,3,4,10-tetrahydro-10-hydroxy-3,3-dimethylpyrimido[1,2-a]indole 1-Benzyloxy-4-bromobutane (6.77 g) was added to magnesium turnings (0.90 g) in diethyl ether (15 ml) under nitrogen. Addition of a small volume of 1,2-dichloroethane followed by gentle warming initiated the reaction. The mixture was heated at reflux for a further 0.5 hour, cooled in an ice bath, then a solution of 3,4-dihydro-3,3-dimethylpyrimido[1,2-a]indol-10(2H)-one (3.0 g) in dry 1,2-dichloroethane (50 ml) added dropwise to the stirred solution. The ice-bath was removed and after 0.5 hour the solution was poured into aqueous NH$_4$Cl and extracted with chloroform (3×100 ml). The chloroform extracts were dried (MgSO$_4$) and evaporated under reduced pressure to give an oil. Trituration of the oil with ethyl acetate gave a yellow solid (3.78 g), which was recrystallised from ethyl acetate to give the title compound as the free base (2.3 g). Ethereal HCl was added to a solution of the free base in methanol, the solvents removed under reduced pressure and the resulting oil triturated with ether to give the title compound as the hydrochloride (2.15 g) m.p. 147°–150°.

Found: C, 69.4; H, 7.5; N, 6.75%. C$_{24}$H$_{30}$N$_2$O$_2$HCl requires: C, 69.5; H, 7.5; N, 6.75%.

EXAMPLE 6

10-(4-Ethoxybutyl)-2,3,4,10-tetrahydro-10-hydroxy-3,3-dimethylpyrimido[1,2-a]indole 1-Bromo-4-ethoxybutane (9.05 g) was added to a stirred mixture of magnesium turnings (1.22 g) in diethyl ether (20 ml) under nitrogen. The mixture was heated to reflux for a further 0.5 hour, cooled in an ice bath and a solution of 3,4-dihydro-3,3-dimethylpyrimido[1,2-a]indol-10(2H)-one (4.28 g) in dry 1,2-dichloroethane (100 ml) added dropwise. The cooling bath was removed and after 1 hour the solution was poured into saturated aqueous NH$_4$Cl (200 ml) and extracted with chloroform (3×100 ml). The extracts were dried (MgSO$_4$) and evaporated under reduced pressure to give an oil. Trituration with ethyl acetate gave a solid (6.0 g) which was recrystallised from ethyl acetate and washed with ether to give the title compound as the free base, yellow crystals (4.86 g). Ethereal HCl was added to a solution of the free base in methanol, the solvents removed under reduced pressure and the gum triturated with ether to give the title compound as the hydrochloride (3.96 g), m.p. 155°-6°.

Found: C, 64.4; H, 8.6; N, 7.9%. $C_{19}H_{28}N_2O_2HCl$ requires: C, 64.7; H, 8.3; N, 7.9%.

EXAMPLE 7

2,3,4,10-Tetrahydro-10-hydroxy-10-(3-methoxybutyl)-pyrimido[1,2-a]indole

A Grignard reagent prepared from magnesium (1.15 g) and 1-bromo-3-methoxybutane (7.93 g) in dry ether (35 ml) was treated dropwise over 30 minutes with a solution of 3,4-dihydropyrimido[1,2-a]indol-10(2H)-one (4.27 g) in dry dichloroethane (20 ml) at 0° under an atmosphere of $N_2$. After warming to room temperature the solution was poured into a mixture of saturated aqueous $NH_4Cl$ (100 ml) and ice (100 g), and extracted with chloroform (3×130 ml). The extracts were washed with water (300 ml), dried ($MgSO_4$), and evaporated in vacuo to give an orange solid (6.64 g) which was triturated with ethyl acetate (5 ml) to give the product free base as pale yellow crystals (4.27 g). The solid was suspended in methanol (10 ml), acidified with $Et_2O$-HCl (ca. 8 ml), and the resulting solution evaporated in vacuo to give the title compound as the hydrochloride (4.85 g), pale yellow crystals, m.p. 200°-204° (dec.)

Found: C, 61.7; H, 7.7; N, 8.7% $C_{16}H_{22}N_2O_2.HCl$ requires C, 61.8; H, 7.5; N, 9.0%.

EXAMPLE 8

10-Hydroxy-10-(3-methoxy-2-methylpropyl)-2,3,4,10-tetrahydropyrimido[1,2-a]indole 1-Bromo-3-methoxy-2-methylpropane (10.02 g) in ether (50 ml) was added dropwise over 20 minutes to magnesium turnings (1.46 g) in ether (10 ml). The mixture was stirred under argon at room temperature for 30 minutes, cooled to 0° and 3,4-dihydropyrimido[1,2-a]indol-10(2H)-one (3.72 g) in dry 1,2-dichloroethane (20 ml) added dropwise over 20 minutes. The solution was stirred under argon at 0° for 1 hour, poured onto a swirling mixture of ice (100 ml) and saturated aqueous ammonium chloride (60 ml). The mixture was stirred for 20 minutes and concentrated in vacuo. The aqueous residue was extracted with chloroform (3×100 ml). The extracts were dried ($Na_2SO_4$) and concentrated in vacuo. Ether (20 ml) was added and the product was filtered and recrystallised from ethyl acetate to give the title compound as the free base (2.85 g), m.p. 162°-167° C. The free base was acidified with ethereal HCl to give the title compound as the hydrochloride, m.p. 244° (dec.).

Found: C, 61.70; H, 7.70; N, 8.80% $C_{16}H_{22}N_2O_2.HCl$ requires: C, 61.85; H, 7.45; N, 9.0%.

EXAMPLE 9

10-Hydroxy-10-(4-ethoxybutyl)-2,3,4,10-tetrahydropyrimido[1,2-a]indole

Ether (10 ml) and a few drops 4-bromo-1-ethoxybutane were added to magnesium turnings (1.46 g). After the reaction started, the remainder of the 4-bromo-1-ethoxybutane (total 10.86 g) in ether (50 ml) was added dropwise over 20 minutes. The mixture was stirred under argon at room temperature for 30 minutes, cooled to 0° C. over 30 minutes and 3,4-dihydropyrimido[1,2-a]indol-10(2H)-one (3.72 g) in dry 1,2-dichloroethane (20 ml) added dropwise over 20 minutes. The solution was stirred under argon at 0° C. for 1 hour, poured onto a swirling mixture of ice (100 ml) and saturated aqueous ammonium chloride (60 ml), and the mixture stirred for a further 20 minutes. The mixture was concentrated in vacuo and the aqueous residue extracted with chloroform (3×100 ml). The extracts were dried ($Na_2SO_4$) and concentrated in vacuo. Ether (20 ml) was added and the product was filtered and recrystallised from ethyl acetate to give the title compound as the free base (2.99 g), m.p. 123°-124° C. The free base was acidified with ethereal HCl to give the title compound as the hydrochloride, m.p. 189°-190° C.

Found: C, 63.25; H, 7.5; N, 8.6%. $C_{17}H_{24}N_2O_2.HCl$ requires: C, 62.85; H, 7.75; N, 8.6%.

EXAMPLE 10

10-Hydroxy-10-(4-methoxybutyl)-2,3,4,10-tetrahydropyrimido[1,2-a]indole

Ether (60 ml) and 4-bromo-1-methoxy-butane (10.2 g) were added to magnesium turnings (1.46 g). After formation of the Grignard reagent, the mixture was cooled to 0° and 3,4-dihydropyrimido[1,2-a]indol-10(2H)-one (3.72 g) in dry 1,2-dichloroethane (20 ml) added dropwise over 20 minutes. The solution was stirred under argon at 0° C. for 1 hour, poured onto a swirling mixture of ice (100 ml) and saturated aqueous ammonium chloride (60 ml) and the mixture was stirred for a further 20 minutes. The mixture was concentrated in vacuo and the aqueous residue extracted with chloroform (3×100 ml). The extracts were dried ($Na_2SO_4$) and concentrated in vacuo. Ether (20 ml) was added and the product was filtered and recrystallised from ethyl acetate to give the title compound or the free base (3.55 g), m.p. 128°-139° C. The free base was acidified with ethereal HCl to give the title compound as the hydrochloride, m.p. 178°-179° C.

Found: C, 61.55; H, 7.55; N, 8.80% $C_{16}H_{22}N_2O_2.HCl$ requires: C, 61.85; H, 7.45; N, 9.0%.

EXAMPLE 11

10-Hydroxy-10-(3-hydroxy-1-propynyl)-2,3,4,10-tetrahydropyrimido[1,2-a]indole (1) 2-(3-Propynyloxy)-3,4,5,6-tetrahydropyran (9.25 g) in ether (100 ml) was added dropwise to a solution of ethyl magnesium bromide (from bromoethane 5.99 g and magnesium 1.6 g) in ether (60 ml) with stirring under an argon atmosphere. After stirring for 30 minutes, the reaction was cooled to 0° C. and 3,4-dihydropyrimido[1,2-a]indol-10(2H)-one (9.31 g) in dry 1,2-dichloroethane (40 ml) was added over 50 minutes. The mixture was stirred under argon at 0° C. for 1 hour and at room temperature for 17 hours. Dry THF (160 ml) was added and the mixture was refluxed for 2 hours. After cooling the mixture was poured onto a mixture of ice (600 ml) and saturated aqueous ammonium chloride (65 ml) and concentrated to a small volume in vacuo. The residue was extracted with chloroform (3×200 ml), washed with brine (100 ml), dried ($Na_2SO_4$) and concentrated in vacuo to give crude 10-hydroxy-10-[3-(2-(3,4,5,6-tetrahydro-2H-pyranyloxy))prop-1-ynyl]-2,3,4,10-tetrahydropyrimido[1,2-a]indole. The product was purified by chromatography on silica eluting with methanol/chloroform (1:20, 1:10). The addition of ether (30 ml) induced crystallisation. Recrystallisation from ethyl acetate gave the pure product as the free base (6.16 g) m.p. 173°-175° C.

Found: C, 69.85; H, 7.10; N, 8.40%. $C_{19}H_{22}N_2O_3$ requires: C, 69.90; H, 6.80; N, 8.60%.

(2) Ethanolic hydrogen chloride (5 ml) was added to a suspension of 10-hydroxy-10-[3-(2-(3,4,5,6-tetrahydro-2H-pyranyloxy))prop-1-ynyl]-2,3,4,10-tetrahydropyrimido[1,2-a]indole (3.0 g) in ethanol (30 ml). The solution was concentrated in vacuo and the product was recrystallised from ethanol to give the title compound as the hydrochloride (2.0 g), m.p. 194° C. dec.

Found: C, 60.55; H, 5.50; N, 10.00%. $C_{14}H_{14}N_2O_2 \cdot HCl$ requires: C, 60.35; H, 5.40; N, 10.05%.

EXAMPLE 12

7-Chloro-10-hydroxy-10-(3-methoxybutyl)-2,3,4,10-tetrahydropyrimido[1,2-a]indole (1) 7'-Chloro-2',3',4',10'-tetrahydrospiro[1,3-dioxolane-2,10'-pyrimido(1,2-a)indole] (5.71 g) was added to cooled 98% sulphuric acid (30 ml) with stirring. The solution was then poured on to ice (300 ml) and basified to pH9 with conc. ammonia solution. The resulting suspension was stirred with chloroform (100 ml) and, after separation, the aqueous phase was exhaustively extracted with further chloroform. Evaporation of the combined, dried ($MgSO_4$) extracts left a brownish orange solid which was crystallised from benzene-cyclohexane, giving 7-chloro-3,4-dihydropyrimido[1,2-a]indol-10(2H)-one as orange crystals (3.06 g), darkening above 160° and melting from 168°-170° with decomposition.

Found: C, 59.6; H, 4.2; N, 12.5%. $C_{11}H_9ClN_2O$ requires: C, 59.9; H, 4.1; N, 12.7%.

(2) A solution of 1-bromo-3-methoxybutane (2.0 g) in dry ether (20 ml) was added dropwise under a nitrogen atmosphere to magnesium turnings (0.3 g) at such a rate as to maintain gentle reflux. After 0.5 hour the reaction mixture was cooled and a solution of 7-chloro-3,4-dihydropyrimido[1,2-a]indol-10(2H)-one (1.0 g) in dry 1,2-dichloroethane (50 ml) was added dropwise. After stirring the reaction mixture for one hour at room temperature it was cooled and excess saturated ammonium chloride solution was added dropwise. The organic phase was separated and the aqueous phase was extracted with chloroform. The extracts were combined with the organic phase, dried ($MgSO_4$) and the solution evaporated in vacuo to leave an oil which was triturated with ether to give a solid. Recrystallisation from ethyl acetate gave the title compound as crystals m.p. 146.5°-148°. A solution of these crystals in warm propan-2-ol was treated with ethereal hydrogen chloride. Evaporation in vacuo followed by recrystallisation from propan-2-ol gave the title compound as the hydrochloride, colourless needles, m.p. 226°-8°.

Found: C, 55.84; H, 6.10; N, 8.02% $C_{16}H_{21}ClN_2O_2HCl$ requires: C, 55.65; H, 6.38; N, 8.12%.

EXAMPLE 13

9-Chloro-10-hydroxy-10-(3-methoxybutyl)-2,3,4,10-tetrahydropyrimido[1,2-a]indole (1) 9'-Chloro-2',3',4',10'-tetrahydrospiro[1,3-dioxolane-2,10'-pyrimido(1,2-a)indole] (6.58 g) was added to cooled 98% sulphuric acid (35 ml) with stirring until complete solution was achieved (approx. 2 hours). The solution was poured on to ice (400 ml) and basified to pH9 with conc. ammonia solution. The resulting suspension of the product was stirred with chloroform (100 ml), and after separation, the aqueous phase was exhaustively extracted with further chloroform. Evaporation of the combined, dried ($MgSO_4$) extracts left a brownish orange solid (4.83 g) which was crystallised from benzene to give 9-chloro-3,4-dihydropyrimido[1,2-a]indol-10(2H)-one as dark orange prisms (3.16 g) darkening above 165° and melting at 170° with decomposition.

Found: C, 59.75; H, 4.1; N, 12.0%. $C_{11}H_9ClN_2O$ requires: C, 59.9; H, 4.1; N, 12.7%.

(2) A solution of 1-bromo-3-methoxybutane (6.0 g) in dry ether (20 ml) was added dropwise under a nitrogen atmosphere to magnesium turnings (0.9 g) at such a rate as to maintain gentle reflux. After stirring at reflux for 0.5 hour the reaction mixture was chilled in ice and a solution of 9-chloro-3,4-dihydropyrimido[1,2-a]indol-10(2H)-one (3.5 g) in dry 1,2-dichloroethane (100 ml) was added dropwise. After stirring the reaction mixture for one hour at room temperature it was cooled and excess saturated ammonium chloride solution was added dropwise. The organic phase was separated and the aqueous phase was extracted with chloroform. The extracts were combined with the organic phase, dried ($MgSO_4$) and the solution evaporated under reduced pressure to leave an oil which was triturated with ether to give a solid. Recrystallisation from ethyl acetate gave the title compound as colourless needles m.p. 164°-5°. Treatment of a solution of these needles in methanol with ethereal hydrogen chloride, followed by evaporation in vacuo gave a solid which was recrystallised from propan-2-ol to give the title compound as the hydrochloride, colourless crystals (2.81 g) m.p. 264°-5°.

Found: C, 55.29; H, 6.71; N, 7.63%. $C_{16}H_{21}ClN_2O \cdot HCl$ requires: C, 55.65; H, 6.38; N, 8.12%.

EXAMPLE 14

10-Hydroxy-10-(3-hydroxypropyl)-2,3,4,10-tetrahydropyrimido[1,2-a]indole (1) A suspension of 10-hydroxy-10-[3-[2-[3,4,5,6-tetrahydro-2H-pyranoxy]]prop-1-ynyl]-2,3,4,10-tetrahydropyrimido[1,2-a]indole (3.14 g) in ethyl acetate (160 ml) was hydrogenated at 2-4 atm over 5% Pd/C (1.063 g) at room temperature for 6 h. The mixture was filtered through Kieselguhr and the filtrate was concentrated in vacuo to give a yellow orange foam. Ether (30 ml) was added and the crystalline product was collected to give 10-hydroxy-10-[3-[2-(3,4,5,6-tetrahydro-2H-pyranyloxy)propyl]-2,3,4,10-tetrahydropyrimido[1,2-a]indole (2.44 g), m.p. 105°-123° C.

Found: C, 68.75; H, 8.30; N, 8.85; $C_{19}H_{26}N_2O_3$ requires: C, 69.05; H, 7.95; N, 8.50%.

(2) A suspension of 10-hydroxy-10-[3-[2-(3,4,5,6-tetrahydro-2H-pyranyloxy)]propyl]-2,3,4,10,tetrahydropyrimido[1,2-a]indole (2.4 g) in ethanol (25 ml) was treated with ethanolic hydrogen chloride (5 ml) and the solution was concentrated in vacuo to give a white foam. The product was crystallised from 20% ethanol/ethyl acetate (20 ml) at −78° C. and the product was collected to give crude title compound as the hydrochloride. The product was dissolved in 2N-HCl (100 ml) and ice (100 ml) and the mixture was basified with concentrated aqueous ammonia at 0° C. The mixture was extracted with chloroform (3×50 ml) and the extracts were dried ($Na_2SO_4$) and concentrated in vacuo. The product was recrystallised from acetonitrile/ethyl acetate to give the title compound as the free base (0.30 g) m.p. 190° C.-193° C. The product was dissolved in ethanolic hydrogen chloride and the solution was concentrated in vacuo. The product was recrystallised from ethanol/ethyl acetate to give the hydrochloride, m.p. 144°–149° C.

Found: C, 58.30; H, 6.65; N, 9.65. C$_{14}$H$_{18}$N$_2$O$_2$.HCl0.25H$_2$O requires: C, 58.55; H, 6.85; N, 9.75%.

We claim:

1. A compound of the formula:

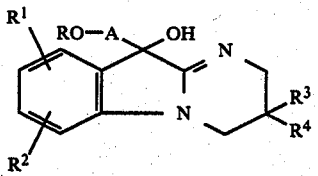

in which

A is alkylene of 1 to 6 carbon atoms;

RO is hydroxy, alkoxy of 1 to 6 carbon atoms, phenylalkoxy of 7 to 12 carbon atoms or substituted phenylalkoxy of 7 to 12 carbon atoms, where the substituent on the phenyl ring is hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

R$^1$ and R$^2$ are, independently, hydrogen, hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

and

R$^3$ and R$^4$ are, independently, hydrogen or alkyl of 1 to 6 carbon atoms;

or a pharmaceutically acceptable salt thereof.

2. A compound of claim 1 in which A is alkylene of 3 to 5 carbon atoms.

3. A compound of claim 1 of the formula:

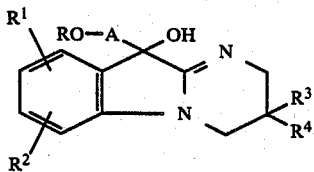

in which

RO is alkoxy of 1 to 6 carbon atoms;

A is alkylene of 3 to 5 carbon atoms;

R$^1$ and R$^2$ are, independently, hydrogen, alkyl of 1 to 4 carbon atoms, alkoxy of 1 to 4 carbon atoms, haloalkyl of 1 to 4 carbon atoms or halo;

R$^3$ and R$^4$ are alkyl of 1 to 4 carbon atoms;

or a pharmaceutically acceptable salt thereof.

4. A compound according to claim 1 which is 3,3-dimethyl-10-hydroxy-10-(4-methoxybutyl)-2,3,4,10-tetrahydropyrimido[1,2-a]indole or a pharmaceutically acceptable acid addition salt thereof.

5. A compound according to claim 1 which is 2,3,4,10-tetrahydro-10-hydroxy-3,3-dimethyl-10-(3-methoxy-2-methylpropyl)pyrimido[1,2-a]indole or a pharmaceutically acceptable acid addition salt thereof.

6. A compound according to claim 1 which is 2,3,4,10-tetrahydro-10-hydroxy-10-(3-methoxybutyl)-3,3-dimethylpyrimido[1,2-a]indole or a pharmaceutically acceptable acid addition salt thereof.

7. A compound according to claim 1 which is 8-chloro-10-hydroxy-10-(4-methoxybutyl)-2,3,4,10-tetrahydropyrimido[1,2-a]indole or a pharmaceutically acceptable acid addition salt thereof.

8. A compound according to claim 1 which is 10-(4-benzyloxybutyl)-2,3,4,10-tetrahydro-10-hydroxy-3,3-dimethylpyrimido[1,2-a]indole or a pharmaceutically acceptable acid addition salt thereof.

9. A compound according to claim 1 which is 10-(4-ethoxybutyl)-2,3,4,10-tetrahydro-10-hydroxy-3,3-dimethylpyrimido[1,2-a]indole or a pharmaceutically acceptable acid addition salt thereof.

10. A compound according to claim 1 which is 2,3,4,10-tetrahydro-10-hydroxy-10-(3-methoxybutyl)-pyrimido[1,2-a]indole or a pharmaceutically acceptable acid addition salt thereof.

11. A compound according to claim 1 which is 10-hydroxy-10-(3-methoxy-2-methylpropyl)-2,3,4,10-tetrahydropyrimido[1,2-a]indole or a pharmaceutically acceptable acid addition salt thereof.

12. A compound according to claim 1 which is 10-hydroxy-10-(4-ethoxybutyl)-2,3,4,10-tetrahydropyrimido[1,2-a]indole or a pharmaceutically acceptable acid addition salt thereof.

13. A compound according to claim 1 which is 10-hydroxy-10-(4-methoxybutyl)-2,3,4,10-tetrahydropyrimido[1,2-a]indole or a pharmaceutically acceptable acid addition salt thereof.

14. A compound according to claim 1 which is 7-chloro-10-hydroxy-10-(3-methoxybutyl)-2,3,4,10-tetrahydropyrimido[1,2-a]indole or a pharmaceutically acceptable acid addition salt thereof.

15. A compound to claim 1 which is 9-chloro-10-hydroxy-10-(3-methoxybutyl)-2,3,4,10-tetrahydropyrimido[1,2-a]indole or a pharmaceutically acceptable acid addition salt thereof.

16. A compound according to claim 1 which is 10-hydroxy-10-(3-hydroxypropyl)-2,3,4,10-tetrahydropyrimido[1,2-a]indole or a pharmaceutically acceptable acid addition salt thereof.

17. A method of treating diabetes which comprises administering to a mammal in need thereof a hypoglycemically effective amount of a compound of the formula:

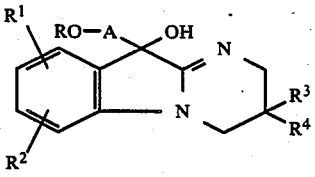

in which

A is alkylene of 1 to 6 carbon atoms;

RO is alkoxy, alkoxy of 1 to 6 carbon atoms, phenylalkoxy of 7 to 12 carbon atoms or substituted phenylalkoxy of 7 to 12 carbon atoms, where the substituent on the phenyl ring is hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

R$^1$ and R$^2$ are, independently, hydrogen, hydroxyl, alkyl of 1 to 6 carbon atoms, alkoxy of 1 to 6 carbon atoms, haloalkyl of 1 to 6 carbon atoms, halo, amino, alkylamino of 1 to 6 carbon atoms or dialkylamino of 2 to 12 carbon atoms;

and

R$^3$ and R$^4$ are, independently, hydrogen or alkyl of 1 to 6 carbon atoms;

or a pharmaceutically acceptable salt thereof.

* * * * *

UNITED STATES PATENT AND TRADEMARK OFFICE
CERTIFICATE OF CORRECTION

PATENT NO. : 4,784,996

DATED : November 15, 1988

INVENTOR(S) : Alan C. White, Ian A. Cliffe, Richard S. Todd

It is certified that error appears in the above-identified patent and that said Letters Patent is hereby corrected as shown below:

Column 4, line 41, delete "3-bromiopropyl" and insert -- 3-bromopropyl --. Column 6, line 62, after "1.2 g" delete the opening bracket " ( " and close the bracket by inserting -- ) --. Column 14, line 52, delete "alkoxy" first occurence, and insert -- hydroxy --.

Signed and Sealed this

Eighth Day of August, 1989

Attest:

DONALD J. QUIGG

*Attesting Officer*     *Commissioner of Patents and Trademarks*